United States Patent [19]

Koutrouvelis

[11] Patent Number: 5,308,352
[45] Date of Patent: * May 3, 1994

[54] STEREOTACTIC DEVICE

[76] Inventor: Panos G. Koutrouvelis, 1201 Ballantrae La., McLean, Va. 22101

[*] Notice: The portion of the term of this patent subsequent to Sep. 10, 2008 has been disclaimed.

[21] Appl. No.: 535,653

[22] Filed: Jun. 11, 1990

Related U.S. Application Data

[63] Continuation-in-part of Ser. No. 437,605, Nov. 17, 1989, Pat. No. 5,047,036.

[51] Int. Cl.$^5$ .............................................. A61B 19/00
[52] U.S. Cl. .................................. 606/130; 606/108; 604/116
[58] Field of Search ............. 606/53, 54, 56, 87, 606/96, 102, 130, 108; 604/116

[56] References Cited

U.S. PATENT DOCUMENTS

| | | |
|---|---|---|
| 2,238,323 | 4/1941 | Hollingsworth . |
| 3,021,842 | 2/1962 | Flood . |
| 3,115,140 | 12/1963 | Volkman .............................. 606/130 |
| 3,955,558 | 5/1976 | Fuisz . |
| 4,332,248 | 6/1982 | DeVitis . |
| 4,350,159 | 9/1982 | Gouda . |
| 4,592,352 | 6/1986 | Patil ..................................... 606/130 |
| 4,638,798 | 1/1987 | Shelden et al. ...................... 606/130 |
| 4,638,799 | 1/1987 | Moore . |
| 4,653,509 | 3/1987 | Oloff et al. .......................... 606/130 |
| 4,706,665 | 11/1987 | Gouda ................................. 606/130 |
| 4,733,661 | 3/1988 | Palestrant .......................... 606/108 |
| 4,750,487 | 6/1988 | Zanetti . |
| 4,841,967 | 6/1989 | Chang et al. ........................ 606/130 |
| 4,875,478 | 10/1989 | Chen .................................... 606/130 |

FOREIGN PATENT DOCUMENTS

1251894 8/1986 U.S.S.R. ............................... 606/130

Primary Examiner—Stephen C. Pellegrino
Assistant Examiner—Glenn K. Dawson

[57] ABSTRACT

A stereotactic device of simplified structure, adaptable to align and precisely orient a variety of medical devices, such as differently sized needles, cannulas, and guide wires, into the human body for procedures, such as tumor biopsies, percutaneous discectomies, cyst aspirations, and tumor localizations, is described. The stereotactic device is adapted for use in combination with a stereotactic bridge which includes a span rotatable on its horizontal axis and movably affixed to a C.T. scan table or an X-ray table by a positioning mechanism that provides for both vertical and horizontal movement of the span. The stereotactic device interacts with a C.T. scanner to achieve accurate placement of the selected medical device. Use of the stereotactic bridge allows alignment of the medical device in sagittal orientation with a high degree of accuracy. The stereotactic device is organized so as to allow a user to introduce accurately the medical device through a sterile field into the human body at a preselected angle. The stereotactic device includes a base, a leg normal to the base, a carrier for the medical device, and markings on the leg. The carrier for the medical device also has a radial portion, a retainer for the medical device, and a lock for fixing the medical device at a selected position.

20 Claims, 6 Drawing Sheets

STEREOTACTIC DEVICE

This application is a continuation-in-part of application Ser. No. 07/437,605, filed Nov. 17, 1989, now U.S. Pat. No. 5,047,036.

BACKGROUND OF THE INVENTION

1. Field of The Invention

The present invention relates to a stereotactic device of simplified structure that is adaptable to align and precisely orient a variety of medical devices such as differently sized needles, cannulas and guide wires into the human body for procedures such as tumor biopsies, percutaneous discectomies, cyst aspirations and tumor localizations. The device of the present invention is adapted for use in combination with a stereotactic bridge comprised of a span rotatable on its horizontal axis and movably affixed to a C.T. scan table or X-ray table by positioning means. The positioning means allows vertical and horizontal movement of the span relative to said tables. The embodiment of the present invention relating to the combination of stereotactic device and bridge provides enhanced accuracy of placement and orientation of the medical device and avoids deviation during insertion attributable to hand movement. The device is interactive with a C.T. scanner to achieve accurate placement of the oriented medical device. The embodiments of the invention involving the use of the stereotactic bridge allow alignment of medical devices in sagittal axial and corona, orientation with a high degree of accuracy. Verification of positioning using the bridge can be accomplished in a facile manner.

2. Description of the Related Art

The need for facilitating subcutaneous injections and orienting the insertion of cannulas or needles with precision in surgical procedures has given rise to the development of numerous devices adapted for such purposes.

An early device for facilitating subcutaneous injection is described in U.S. Pat. No. 3,021,842. A locking ball and socket arrangement is disclosed and is used for positioning a needle at a desired angle. To lock the ball in the socket at the preselected angle, the patentee provided a ball-engaging ring that was threaded on the socket.

More recently, after the advent of C.T. scanning, new devices for orienting and inserting cannulas or needles have been developed.

C.T. scanners are commonly used to provide doctors with cross-sectional internal pictures of a patient. Through the use of C.T. scanner technology, physicians are able to accurately place biopsy needles and drainage catheters into preselected areas of the body with a high degree of success.

C.T. scanners are capable of measuring a proposed trajectory for a biopsy needle or drainage catheter to within 0.1 millimeters with respect to depth, and within 0.1 degree with respect to angular orientation.

A hand-held needle guidance device which is suitable to accurately and easily use C.T. generated information to position a biopsy needle or drainage catheter relative to a patient's body is described in U.S. Pat. No. 4,733,661. The described guidance device utilizes a needle support arm hinged at the end of a planar base. The arm is oriented by protractor means also situated at the hinged end of the base. A wing nut arrangement is used to lock the pivoting arm at a predetermined angle relative to the planar base. The planar base is horizontally oriented by a circular bubble level on the base.

In apposition to the simple hand-held guidance device of U.S. Pat. No. 4,733,661, one finds in the art highly complex C.T. scanner guided stereotactic brain surgery devices utilizing skull mounted frames with associated complex positioning instruments. Such instruments, as pointed out in U.S. Pat. No. 4,733,661, are well-known in the art, such art being well referenced in U.S. Pat. No. 4,733,661.

A C.T. scanner guided stereotactic brain surgery instrument described in U.S. Pat. No. 4,350,159 is used to precisely insert an electrode in the brain of a patient for treatment of nervous disorders. The orientation of the inserted electrode at an angle to the plane formed by the frame is achieved utilizing a semicircular rotatable arc mounted on the frame onto which a movable electrode carrier can be locked. A separate protractor is used to orient the electrode carrier. For drilling the hole through which the electrode is inserted, the arc is rotated part of the way.

SUMMARY OF THE INVENTION

The present invention achieves movement of a medical device along an arc defined by an arcuate slot/opening in a protractor which operates as a means of both orienting and supporting a carrier which rides within the slot. The carrier can be locked into position along the arc defined by a slot at any preselected angle.

In accordance with the present invention, a T-shaped or L-shaped stereotactic device of simple structure allows a user to accurately introduce a medical device within a body at a preselected angle. The device is adapted for interactive use with a C.T. scanner and on a patient horizontally supported on the surface of a C.T. scan table. In one embodiment of the invention, the stereotactic device comprises a base having an upper surface exposed when the stereotactic device is in use and a lower surface placed on the body into which the medical device is to be introduced. The base has an opening therein, through which the part of the medical device to be placed within the body can pass unobstructed. The opening may be of any shape or size, provided that the instrument inserted into the patient can be accommodated. The opening defines the sterile field through which the medical device is inserted and therefore the size and placement should be appropriate for the use intended.

In another embodiment of the invention adapted to facilitate disengagement and removal of the base and leg from the medical device, the opening in the base is formed by cutting out a portion of the base. Such opening is herein, alternatively, referred to as the cutout, cutout portion/opening or cephalic opening, the latter being a coined term referring to an opening in the base that begins at an edge of the base and is open toward the gantry of the C.T. scanner. This opening delimits the sterile field. The term "opening" includes the completely open side of the L-shaped device where the sterile field is delimited by the leg and base thereunder. By using a cutout as the opening, the stereotactic device can be removed by disengaging the carrier for the medical device and removing the stereotactic device away from the locus of insertion in a horizontal direction. A wall normal to the base, suitably the leg of a T-shaped aluminum bar, having an arcuate slot therein, defines a circular segment for angular orientation. The stereotactic device has a carrier for the medical device which is comprised of the following: an arcuate portion which rides within the arcuate slot; retaining means for retaining the medical device in a fixed radial position relative to the arc defined by the arcuate slot and downwardly through the opening in the base; and means for locking said carrier at a fixed position on the arcuate pathway formed by the slot.

There are markings on the wall along said arcuate slot for placement of the retaining means at a preselected point along said arcuate slot whereby the medical device retained thereby can be extended downwardly through the opening and into the body at a preselected angle. There are also markings on the surface and/or edges of said base for orientation of said base on the body.

Where linear markings are utilized to align the stereotactic device of the present invention, suitably one or more marks are scribed on the upper surface of the base and run along at least a portion of the length of the upper surface of the base in parallel with the wall. If extended across the base opening, the extended scribe mark/line would intersect the radial line defined by the pathway through which the medical device, e.g., a needle, is oriented. The linear scribe marks are particularly helpful in alignment of the stereotactic device where the base is made of a transparent material, e.g., a clear plastic such as one of the polycarbonates. Such plastics are among the materials which meet the structural requirements of the stereotactic device of the present invention and can withstand conditions of sterilization.

It has been found that alignment of the stereotactic device, using markings on top of the base, can be facilitated if the edges of the base are beveled. Thus, the edges intersecting the plane formed by the transverse light source of the C.T. scanner are preferably beveled. In accordance with the embodiment of the invention involving beveling the edge of the base, the marking on the top of the base, which is used to orient the stereotactic device, extends angularly within the plane of the image cross-section.

Accordingly, the alignment of the stereotactic device on the laser light beam reference line replicated on the patient can be readily confirmed by the physician by reference to the opposite marked ends. The markings at each end should fall on the reference line on the patient. Where a metallic base, suitably aluminum or some other nontransparent material, is used to fabricate the stereotactic device, beveling of the ends is much preferred, since alignment using the markings at the edges of the bases is facilitated where the mark can be placed adjacent to the reference line.

Where the retaining means is adapted to accommodate a series of differently sized devices, e.g., needles, a series of markings are suitably used, with one marking for orienting the pathway of each needle of varying size.

The center of the circle formed by extending the arcuate segment defined by the arcuate opening should be at a point in the plane formed by the bottom surface of the base.

A leveling means may be associated with the device to aid in orienting the longitudinal axis of the base horizontally. The leveling means suitably is a circular bubble level on the upper surface of the base. The site of the level is preferably situated on top of the horizontal base, on the side of the base extending outwardly from the surface of the leg facing away from the sterile field. The linear markings on the upper surface of said base suitably run along at least a portion of the length of the upper surface of the base in parallel with the surface of the leg. Preferably, the markings extend to the opposed edges of the base normal to the leg. Such edges are most preferably beveled to facilitate alignment of the stereotactic device using a reference line on the patient.

The present invention, as previously noted, is a guidance device for allowing a user to accurately introduce a medical device to a preselected point in a patient's body. The stereotactic device comprises a base including a plate to be placed on and/or supported by the patient's body and an upstanding leg positioned substantially perpendicular to the plate. The plate has an opening through which a lower part of the medical device can pass unobstructed into a predetermined part of the patient's body. The leg has an arcuate slot of a given width cut therethrough and is marked to indicate a preselected angle relative to the predetermined part of the patient's body which is accessible through the opening in the plate. A carrier, which rides within the arcuate slot cut through the leg of the base, carries a means for retaining the medical device in a fixed position relative to the riding means and a means for locking the retaining means at one of the preselected angles relative to the predetermined part of the patient's body. The riding means may be a cylindrical protrusion having a threaded bore therethrough and an outer diameter slightly less than the given width of the arcuate slot cut through the leg. Preferably, the retaining means is comprised of a pair of arms with threaded bores therethrough, spaced from each other at a distance less than the given length of the medical device to assure that said medical device can be held securely in the bores thereof. The locking means typically is comprised of a threaded fastener for engaging the threaded bore through the cylindrical protrusion of the riding means.

One aspect of the present invention comprises the use of the above-described stereotactic device in combination with a stereotactic bridge. The stereotactic bridge functions to both steady the stereotactic device and to assure alignment of the leg wall of the stereotactic device parallel to the plane described by the tomographic cut image.

The stereotactic bridge is adapted for affixation to patient tables typically used for positioning a patient in the gantry of a C.T. scanner or relative to an X-ray machine.

In another embodiment of the invention, stereotactic device placement is facilitated by using same in combination with a stereotactic bridge. The stereotactic bridge is comprised of stanchions and a span which overlies the patient. The span is used to support the stereotactic device. The span can be rotated axially to orient the medical device carried along the arcuate track of the leg of the stereotactic device so that the part inserted into the patient is within the plane of the tomographic cut of the C.T. scanner. The tomographic cut image generated by the C.T. scanner is used to develop the locus of entry and angle of insertion of the medical device. The wall of the leg of the stereotactic device which carries the medical device must be in a plane parallel to the plane of the tomographic cut in order to ensure accurate placement of the medical device.

The stereotactic bridge is comprised of means for positioning the stereotactic device relative to the patient.

The span of the stereotactic bridge is movable in a horizontal plane both towards and away from the gantry. Described in terms relative to the patient's torso, the horizontal movement is from head to foot, although the limits of horizontal movement need not traverse the entire length of the torso.

The means employed for horizontal movement may comprise a slide and guide arrangement along the side of the C.T. scan table. The horizontal guide, typically a metal rail, is parallel to the C.T. scan table surface and is affixed to the fixed support on which the movable table top of the C.T. scan table is carried. The patient is placed on the movable table top in the appropriate position for the medical procedure. The movable table top is used to move the patient into and away from the gantry of the C.T. scanner.

The bridge is movable in a vertical direction to rest the table on the patient's torso at the appropriate height.

The means employed for horizontal movement may comprise a slide and guide array of any configuration and suitably may be square, round or some other shape.

The stereotactic device which rides on the span and can be locked in position at a given point along the length of the span is thus movable side-to-side relative to the patient's torso.

The means employed for side-to-side movement may comprise a slide and guide array of any configuration, square, round or some other shape, or any form of suitable track for movement of the stereotactic device across the patient's body.

The sliding elements of the horizontal, vertical and side-to-side movement means suitably include means for securing the slides in the required positions. Locking means such as set screws, wing bolts, and simple mechanical elements, can be used among others as slide/track locks. The stereotactic bridge architecture is chosen to achieve movement and positioning using simple and reliable mechanisms and the details of specific machine elements selected are such as would be appreciated by one skilled in the art.

In one specific embodiment of the present invention, the stereotactic device includes a guide attachment integral therewith that is comprised of a slide which rides on the span of the stereotactic bridge. Such side-to-side guide and slide arrangement provides the most elementary side-to-side positioning means for the stereotactic device carried by the bridge. The bridge in the alternative may be stabilized and oriented by affixation to the floor. In this embodiment, the movable C.T. scan table top moves and the span remains fixed rather than vice versa.

DETAILED DESCRIPTION OF THE DRAWINGS

Figures 1, 2, 3:
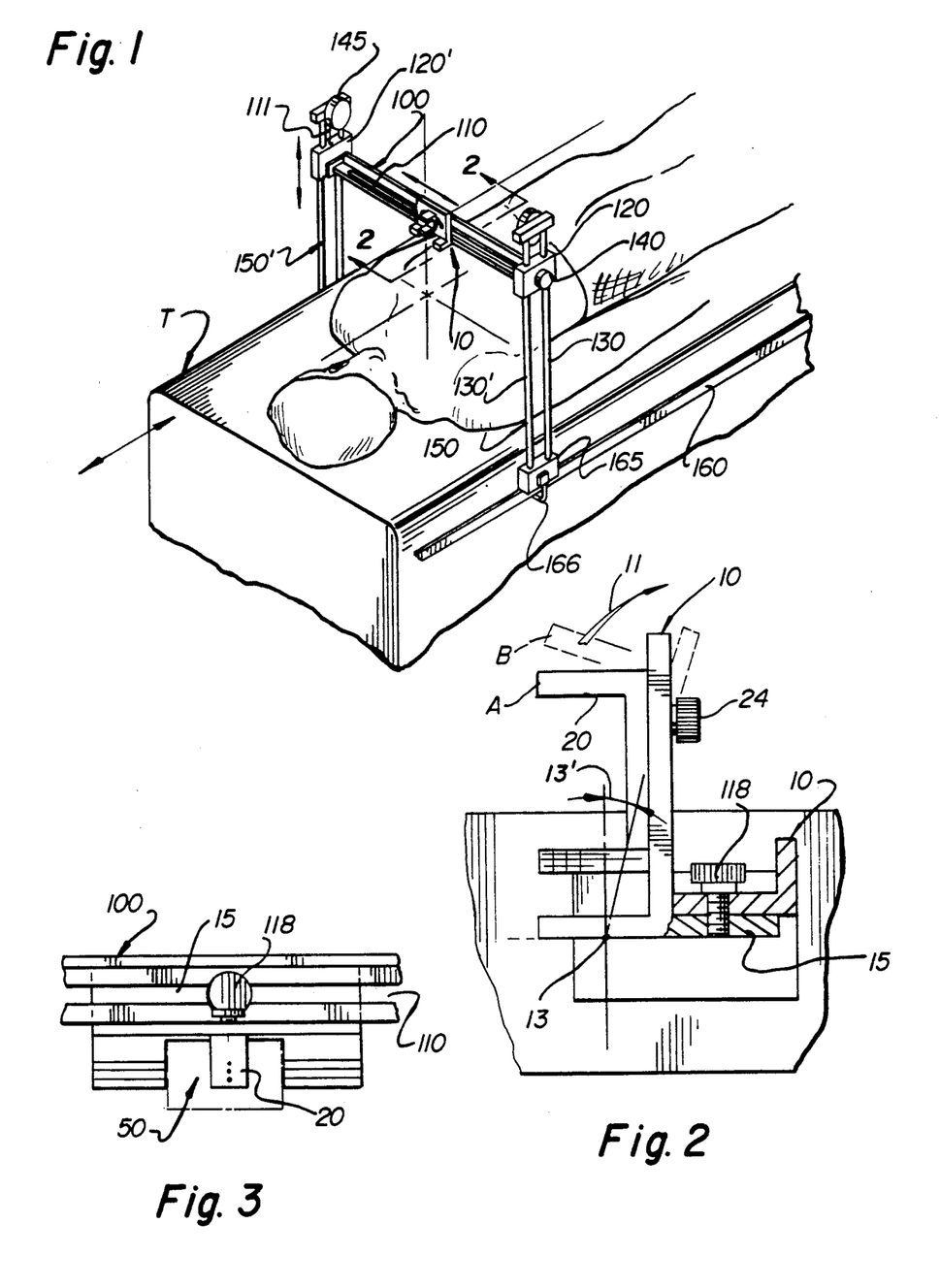
FIG. 1 is a perspective of a first embodiment of the invention involving in combination the stereotactic device and bridge.
FIG. 2 is a sectional view taken along 2—2 of FIG. 1.
FIG. 3 is a top view of FIG. 2.

In FIG. 1, a preferred first embodiment of the invention is shown wherein the stereotactic medical device comprising a guidance device 10 is carried, oriented and stabilized by a stereotactic bridge. The stereotactic bridge is comprised of a span 100 carried by two stanchions 150 and 150'. The bridge is movable horizontally along the length of a C.T. scan table T using a rail guide 160 on which slide 165 supporting linear bearings 130 and 130' is carried. Toggle clamp 166 locks the slide 165 in position after horizontal positioning.

The span 100 is movably carried on the stanchions 150 and 150' by support members 120 and 120'. Vertical positioning of the span 100 is achieved by sliding the support members 120, 120' up and down the linear bearings 130 and 130' of the stanchions 150 and 150'. Up and down movement of the span 100 is facilitated by use of a negator spring or spring balancer 145 attached to the support members 120 and 120' by a retractor cord 111.

Positioning side-to-side across the width of the body/table T is achieved by moving the guidance device 10 in a slot/groove 110 lengthwise along the span 100.

A simple carriage in a locked position is illustrated in FIG. 2, where a thumbscrew 118 is shown in locking engagement with a base 15 of the guidance device 10. As best illustrated in FIG. 3, the thumbscrew 118 serves the dual purpose of a carrier as well as a locking means, sliding along the slot 110 of the span 100.

Figures 4, 5, 6:
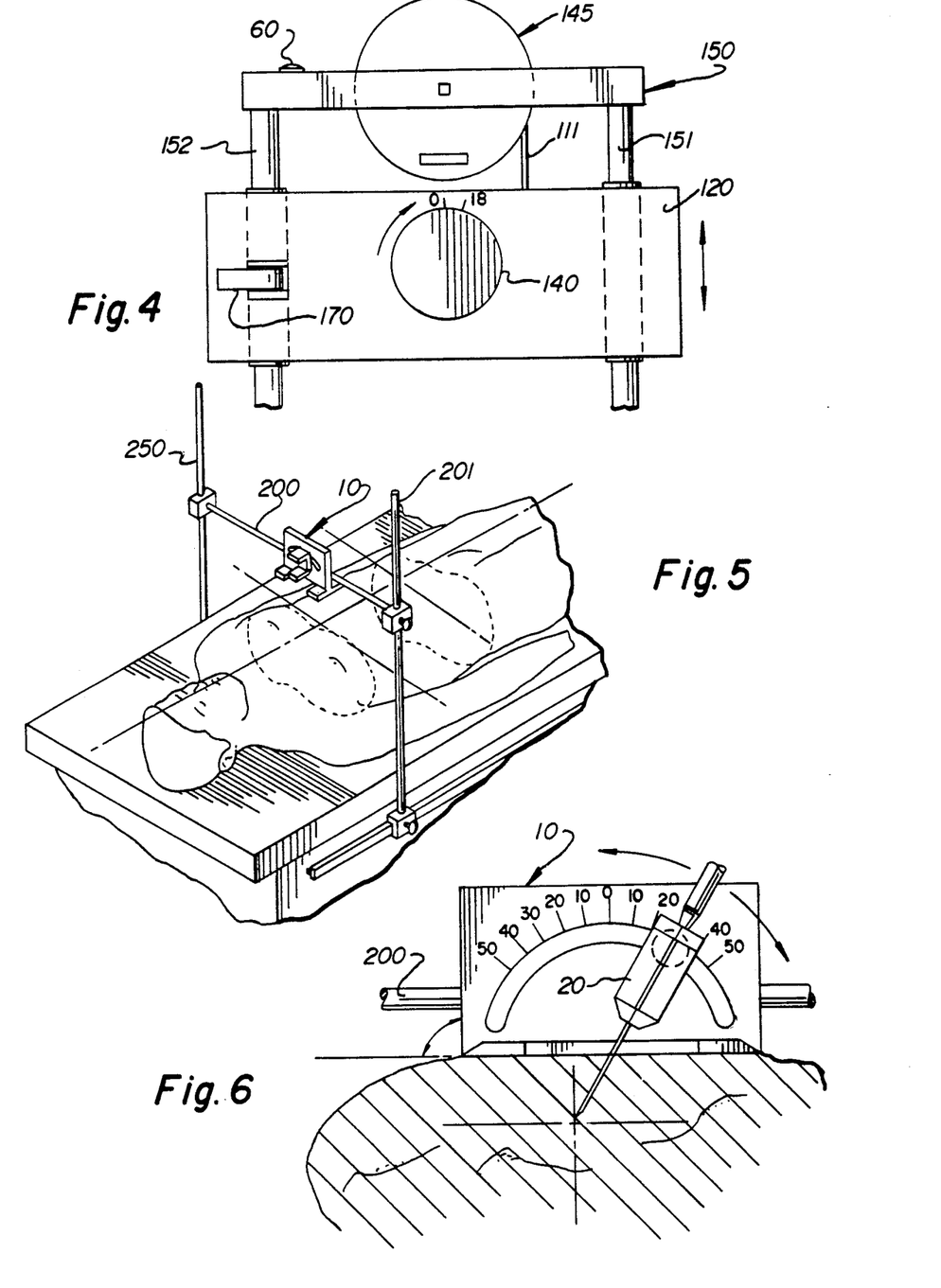
FIG. 4 is a partial view of a top portion of a stanchion illustrating a negator spring and a rider on stanchion rails including a knob which is used to adjust a sagittal angle and a cam lock.
FIG. 5 illustrates a simplified and alternative second embodiment of the combined stereotactic device and bridge.
FIG. 6 is a front view of the device in use showing a partial cross-section of a torso to illustrate insertion of a needle to a predetermined point.

In FIG. 4, one of the support members 120 is shown. Toggle clamp 170 is used to lock the span (not shown) in position on a vertical bearing 152 of the stanchion 150. For this purpose, a more simple arrangement, such as a thumbscrew or another alternative, is suitable.

Knob 140, which is attached to the support member 120, is used to rotate the span (not shown) axially in the direction of the arcuate arrow. The mechanism for this axial rotation can be chosen from any of the typical arrangements allowing angular adjustment. Thus, for this purpose, one may use a mechanism rotatable by the knob 140 which is affixed to a shaft passing through the support member 120 and which also is connected to the bridge.

The specific mechanism and markings for achieving and measuring the axial rotation are matters of choice; however, it should be underscored that, in the preferred embodiment of the present invention, where the stereotactic medical device is to be used for sagittal introduction, as shown in FIG. 2, the axis of rotation 13' of the guidance device should pivot on a centerline which intersects the point of entry 13 of the medical instrument into the body. This feature is illustrated by reference to the two positions A and B of the guidance device 10, only one of which (B) is shown in shadow with the angulation pattern represented by arrow 11.

As shown in FIG. 4, a leveling device, such as a bubble 60, may be used to verify that a cross-brace atop stanchion 150 is perfectly horizontal.

FIG. 5 illustrates a most simple second embodiment of the present invention where the guidance device 10 is carried on a span 200 made from a cylindrical rod and where cylindrical rods are used for stanchions 201 and 250. As can be readily appreciated, the stability of this simplified embodiment suffers because of the potential for movement of the stanchions 201 and 250, if care is not exercised by the user.

Figure 7:
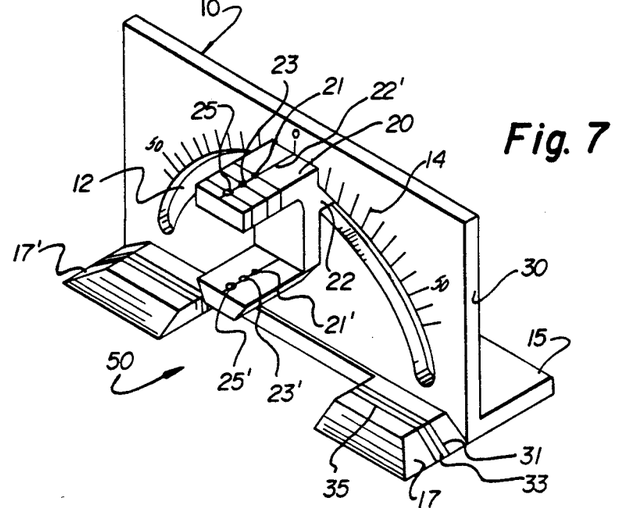
FIG. 7 is a perspective view of the second embodiment of the stereotactic device illustrating the relationship of a needle holder to a cutaway portion defining a sterile field.

In FIG. 7, a preferred structure for the guidance device 10 is shown. This guidance device 10 has an inverted T-shaped cross-section and is comprised of a base 15 with a protractor leg 30 normal thereto.

The protractor leg 30 has a radial slot 12 in which a radial portion 22 of a carrier 20 rides. A first marking 14 along the radial slot 12 and a second marking 22' on the carrier 20 are used for radially aligning the carrier 20 at a preselected sagittal angle. Apertures 21, 23, 25 and 21', 23', 25' are used to retain, as is more clearly shown in FIG. 8, a needle 98 of a syringe 99 along its length in a fixed position on the carrier 20. The apertures are spaced away from the protractor leg 30 and positioned over the cutout portion 50, best shown in FIG. 7. This cutout portion 50 denotes generally the sterile field. The base 15 of the guidance device 10 illustrated in FIG. 7 has beveled edges 17, 17' and markings 31, 33, 35 for aligning the device 10 on the body of the patient.

Figure 8:
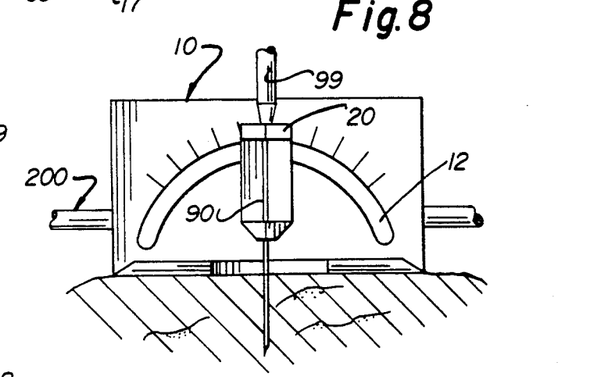
FIG. 8 is a front view of FIG. 7 with the needle in use being inserted vertically.

In FIG. 8, the needle 98 is shown in position on the carrier 20 and inserted into the patient's body. The position shown in FIG. 8 is used where a 90° vertical orientation is required. Insertion at a preselected sagittal angle is illustrated in FIG. 6. A portion of the span 200 of the stereotactic bridge is also shown in both FIGS. 6 and 8.

Figure 9:
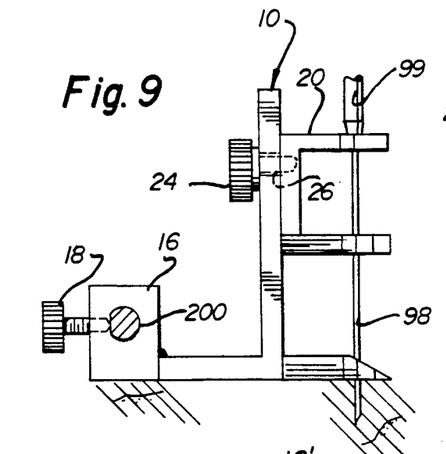
FIG. 9 is a side view of FIG. 8.
Figure 10:
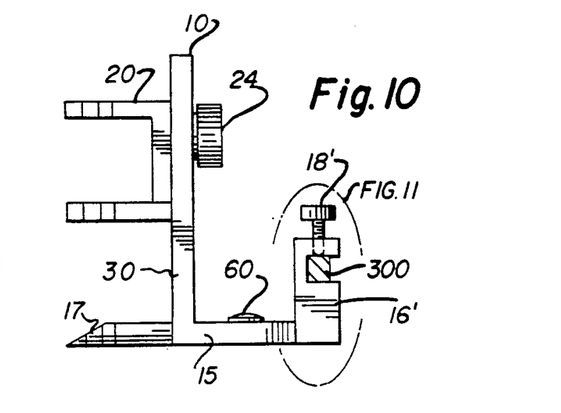
FIG. 10 is an end view illustrating an alternative third embodiment using a rectangular span.

FIGS. 9 and 10 illustrate the use of a first thumbscrew 24 to lock the carrier 20 onto the guidance device 10 in place along the radial slot 12 seen in FIGS. 7 and 8. A threaded portion 26 of the thumbscrew 24 is shown only in FIG. 9. A second thumbscrew 18 that functions as a lock mechanism for the span 200 is passed through a slide member 16 illustrated in FIG. 9.

Figure 11:
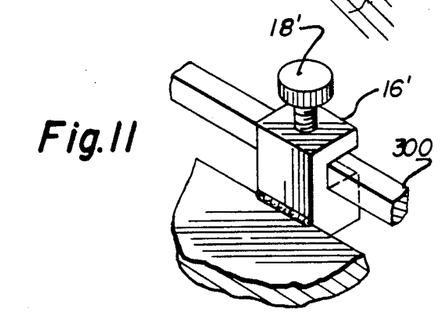
FIG. 11 is a perspective view of a partial section taken from FIG. 10.

In FIGS. 10 and 11, an alternative slide member 16' for use with a span 300 having a square cross-section and a thumbscrew 18' for locking the slide member 16' onto the span 300 are illustrated in a third embodiment. Placement of a bubble leveling means 60 on the guidance device 10 is illustrated in FIG. 10.

Figures 12, 13, 14, 15:
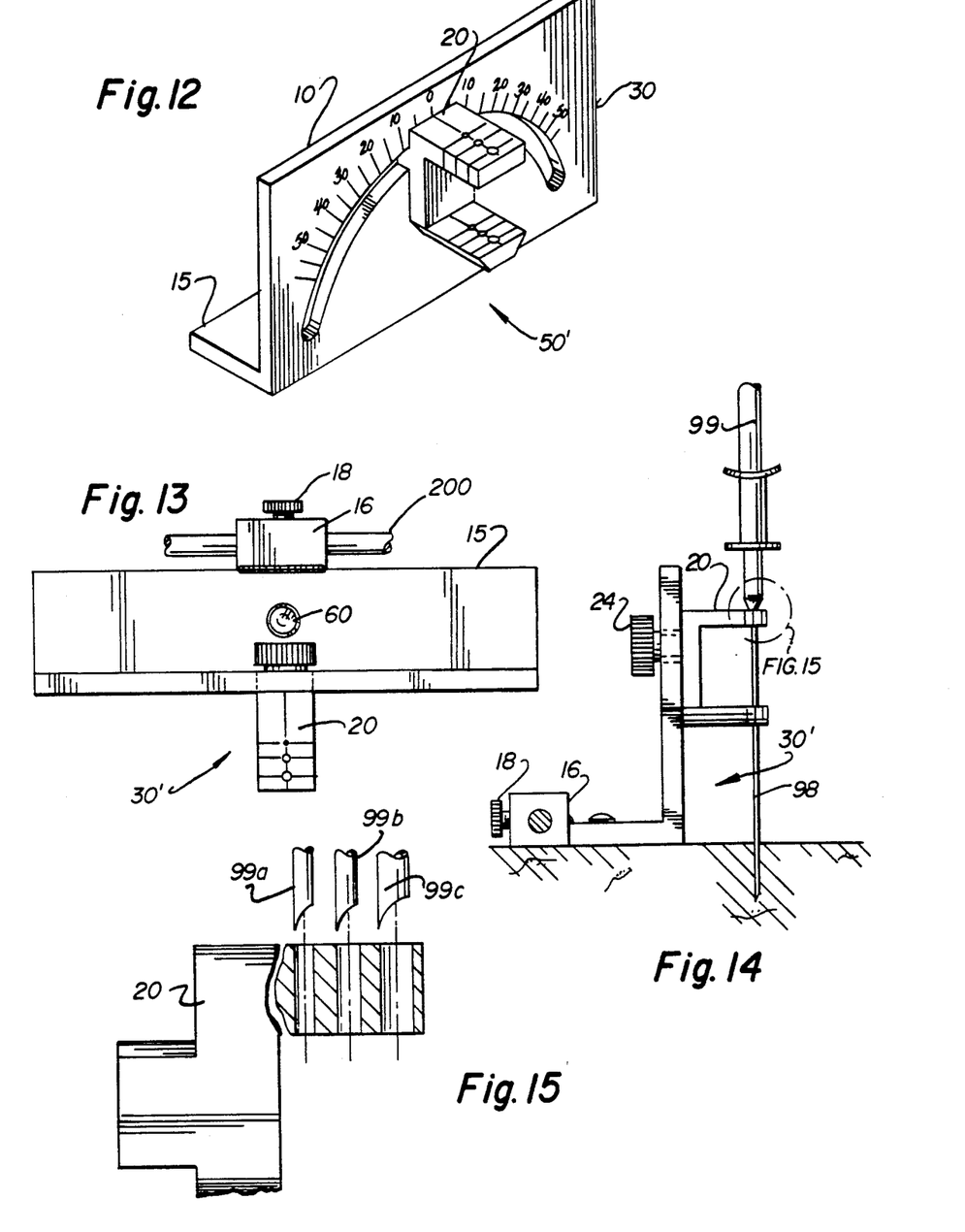
FIG. 12 is a fourth embodiment of the invention wherein an L-shaped stereotactic device is illustrated in a perspective view.
FIG. 13 is a top plan view of the device shown in FIG. 12 and affixed to a cylindrical span.
FIG. 14 is an end view of FIG. 12.
FIG. 15 is a broken away view of a partial section taken from FIG. 14 illustrating the use of variously sized needles.

FIG. 12 illustrates a fourth embodiment having an L-shaped configuration for the guidance device 10 in which the base 15 does not extend, i.e. is entirely cutout, on the sterile side of the protractor leg 30. In other words, a cutout portion 50' covers the entire sterile field. This fourth embodiment is particularly suitable for sagittal orientation where any outcropping of the base 15 on the sterile field side of the protractor leg 30 would either impede or interfere with the axial rotation of the stereotactic bridge and the guidance device 10. FIGS. 13 through 15 illustrate further, using alternative views, the guidance device 10 of the present invention with FIG. 15 indicating an adaptation of the carrier 20 to be used for a variety of syringes of differing diameters, as shown by syringes 99a, 99b and 99c.

Figure 16:
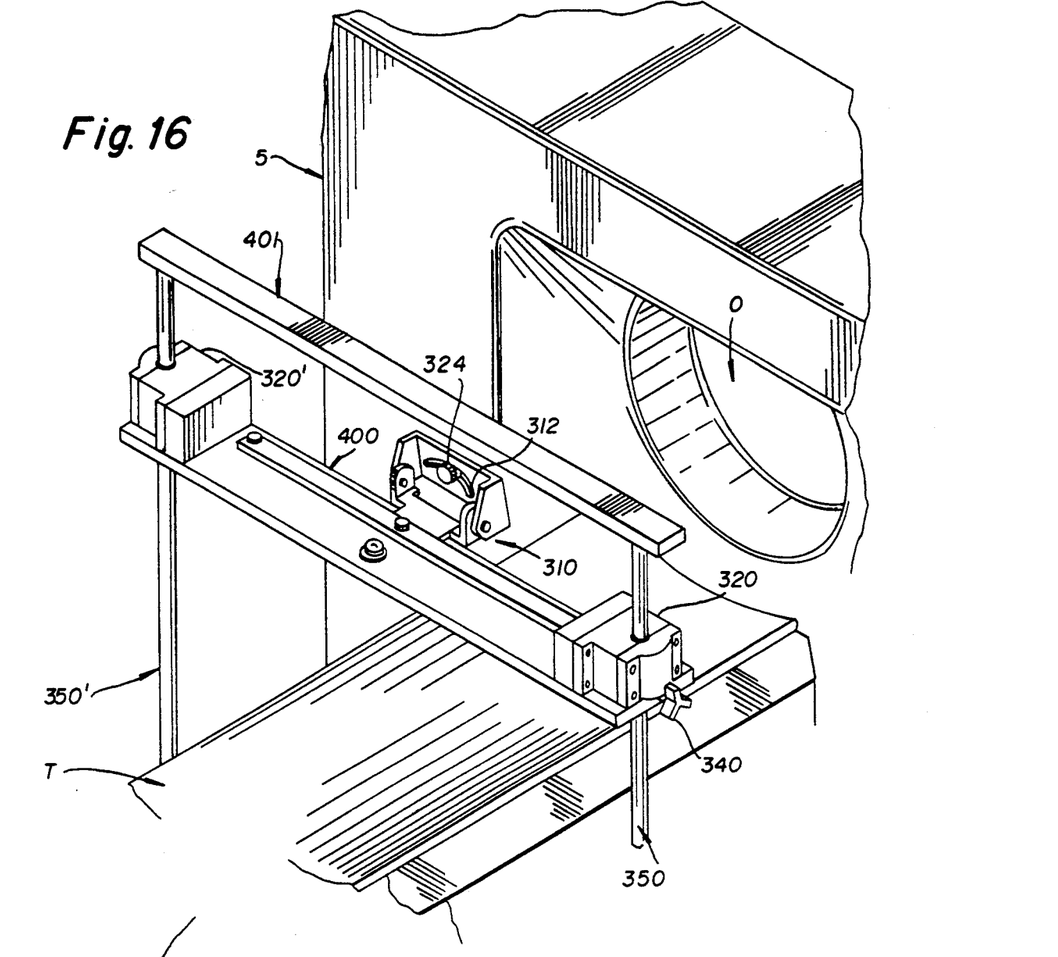
FIG. 16 is a perspective view of a fifth embodiment of the invention involving the stereotactic device and a modified bridge in combination with a C.T. scanner and table.

In FIG. 16, a preferred fifth embodiment of the invention is shown, wherein the stereotactic medical device comprising a guidance device 310 is carried, oriented and stabilized by a stereotactic bridge comprised of a span 400 carried by two stanchions 350 and 350'. The bridge is movable horizontally along the length of the C.T. scan table T using a rail guide (not shown).

The span 400 is movably carried on the stanchions 350 and 350' by support members 320 and 320'. Vertical positioning of the span 400 is achieved for sliding the support members 320 and 320' up and down on the stanchions 350 and 350'. A knob 340, which is attached to the support member 320, is used to secure and tighten the span 400 at a selected position along the stanchions 350 and 350'. A cross-brace 401 is welded to tops of the stanchions 350 and 350' to prevent an operator from inadvertently sliding the support members 320 and 320' over the tops of the stanchions 350 and 350'.

When the stereotactic medical device is placed in a desired position and a patient (not shown) is lying ready on the table T, the table T carries the patient into a gantry opening O in a C.T. scanner S, shown only in FIG. 16.

Figure 17:
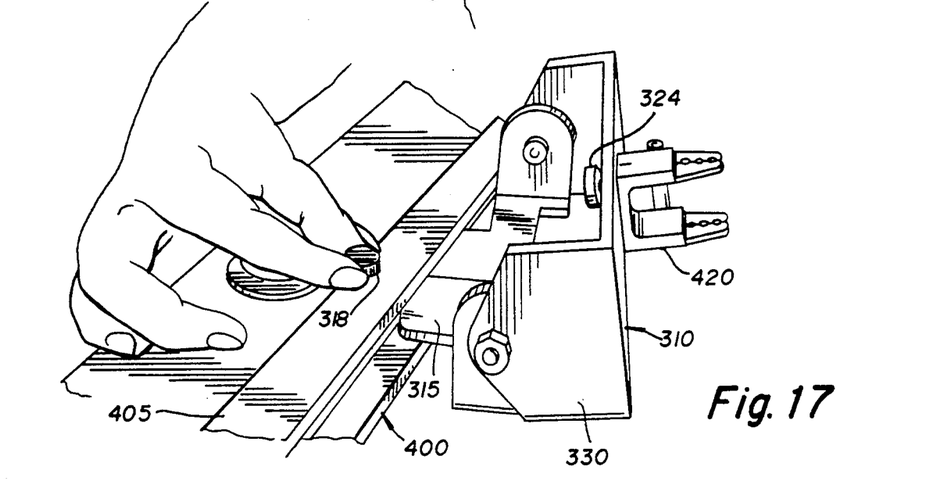
FIG. 17 is a perspective view of the stereotactic device being clamped into position on the modified bridge.

In FIG. 17, positioning side-to-side across the width of the patient's body on the table T is achieved by moving the guidance device 310 lengthwise along the span 400 under a flexible metallic strip 405 that is either tightened or loosened on the span 400 by a plurality of thumbscrews 318, of which only one is shown. The illustrated thumbscrew 318 is shown in the process of lockingly engaging the strip 405 on a base leg 315 of the guidance device 310. In addition to the base leg 315, the guidance device has a rotatable protractor portion 330. Also, as seen in FIG. 17, another thumbscrew 324 locks a carrier 420 onto the guidance device 310 in place along a radial slot 312 (not shown in FIG. 17, but see FIG. 16).

Figure 18:
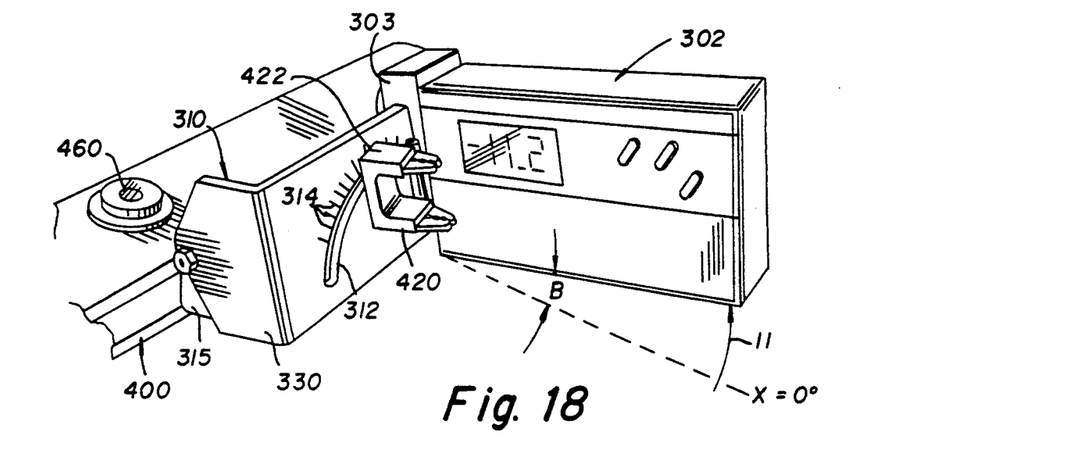
FIG. 18 is a perspective view of the stereotactic device with the angle of axial rotation being measured by an electronic angle measuring device.

In FIG. 18, the protractor portion 330 of the guidance device 310 is seen better. Also, angular rotation of the carrier 420 in the radial slot 312 of the guidance device 310 is determined by reading the alignment of a single marking 422 on the carrier 420 with one of a plurality of markings 314 along the radial slot 312.

Also in FIG. 18, a preferred mechanism for measuring the axial rotation of the guidance device 310 around the span 400 is an electronic protractor 302 manufactured by the Mitutoyo Corp. of Japan. The illustrated protractor 302 is known as Digimatic Model No. 950-313. The rotation of the guidance device 310 around the span 400 is measured in degrees from an abscissa more commonly known as an X-coordinate.

The electronic protractor 302 has a hooked end 303 for securement over the guidance device 310 so that the electronic protractor 302 rotates at the same angle as the guidance device 310.

As illustrated in the example of FIG. 18, the electronic protractor 302 is rotated counterclockwise from the horizon where $X=0°$ to an angle $B=-11.2°$. Compare the angle B in FIG. 18 with the position B in FIG. 2 and note that, in both FIGS. 2 and 18, the angulation pattern is represented by the same arcuate arrow 11.

As shown in FIG. 18, a leveling device, such as a bubble 460, may be used to verify that the span 400 is perfectly horizontal, i.e., positioned where the angle $B=0°$.

Figure 19:
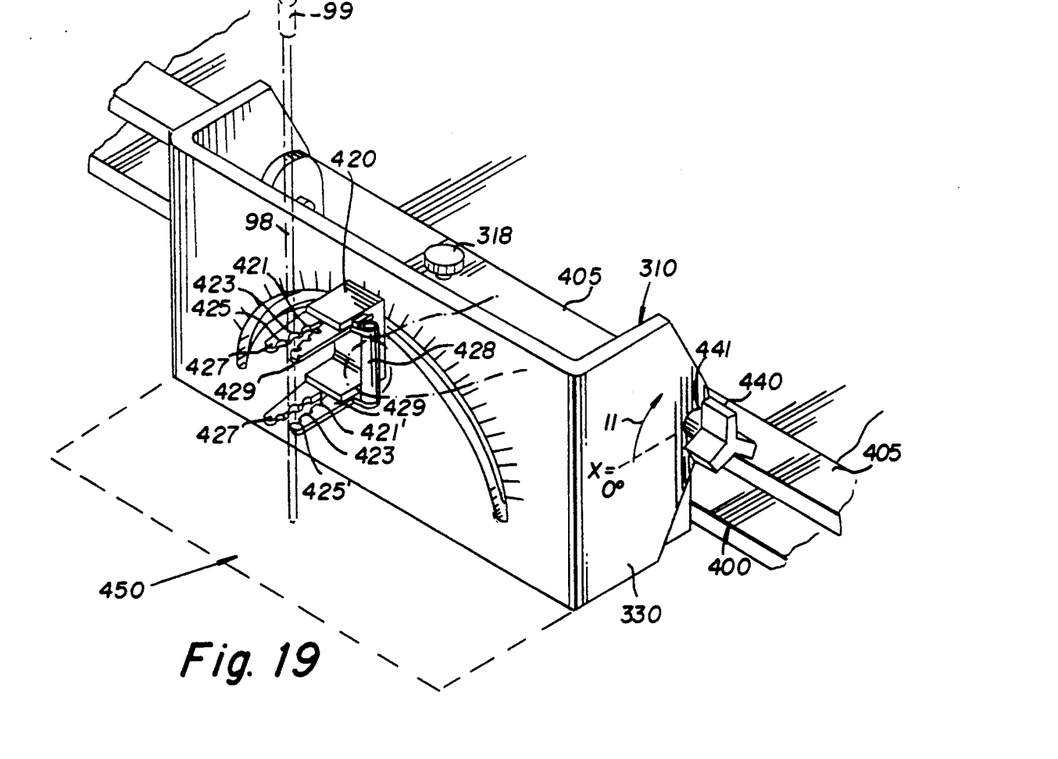
FIG. 19 is a perspective view illustrating in phantom lines the needle in use being inserted vertically.

In FIG. 19, a knob 440, which is attached to the guidance device 310, is either tightened or loosened to allow angular rotation of the protractor portion 330 in the direction of the arcuate arrow 11 about the span 400 which is horizontally oriented at a position where $X=0°$. The knob 440 has a shaft 441 passing through the guidance device 310. Because the thumbscrew 318 tightens the strip 405 down on the leg 315 (not shown in FIG. 19, but refer back to FIG. 17) of the guidance device 310, true horizontal orientation of the leg 315 is maintained.

As also seen in FIG. 19, the carrier 420 has a pair of so-called "alligator-type" clips 427 which will be opened when the operator's thumb presses on a roll pin 428 that separates one hinged jaw 429 of each clip 427 from a fixed jaw thereof. Thus, apertures 421, 423, 425 and 421', 423', 425' are opened to facilitate entry of the needle 98 extending from the syringe 99 into a selected one of the apertures. These apertures are closed around the needle 98 when the operator releases finger pressure on the roll pin 428. The apertures are spaced away from the protractor portion 330 and positioned over a cutout portion 450 that denotes generally the sterile field for inserting the needle 98 at a predetermined point into the body of the patient.

Two modes for using the various embodiments of the sterotactic device will now be described with reference to some of the drawing figures discussed above.

USE OF THE STEREOTACTIC DEVICE IN C.T.-GUIDED DISCECTOMY (HAND-HELD MODE)

A C.T. scan is made of the suspected disc herniation with the scanner S. The patient is placed in the prone position on the scanning table T, prepped, and draped in the usual manner.

The point of entrance of the selected site in the skin, as well as the depth and the angle to be used, is calculated under C.T. guidance in a manner well known to the art as follows:

The table top carrying the patient is moved into the gantry opening O and thin 3-5 mm axial tomographic cuts are obtained by C.T. scan through the herniated disc.

The best tomographic cut is selected and a transverse light beam line identical to the tomographic cut with an X-ray beam is made on the patient and marked on the skin with a colored line.

The point of entrance is marked with a needle 98 and determined by the C.T. scan. The depth and angle are determined by C.T. scan guidance.

Local anesthesia is administered in the skin, muscles, and paravertebral space. A three (3) mm skin incision is made at the selected point of entry for a flexible trocar.

Using the stereotactic device for proper guidance of the trocar, the physician inserts the flexible trocar slightly posteriorly into the nucleus pulposus of the herniated disc. The stereotactic device is placed on the patient and is oriented so that the trocar is introduced into the body in the plane of the cross-section image developed by the C.T. scanner S. This requirement is achieved by aligning the appropriate markings 14 and 22' on the stereotactic device in the plane of trocar travel with the colored line. The colored line is a reference line drawn on the patient that is located within the vertical plane viewed by the C.T. scanner S. A marked trocar is used. Such trocars are marked along their length so that the depth of insertion is readily controlled by observing the reference markings and by inserting the same to the predetermined depth by reference to these markings. The proper position of the flexible trocar is verified again by the C.T. scanner S.

Prior to verification, it is a simple matter, in view of the facile arrangement for disengaging the carrying means, to disengage the carrier 20 and the carried medical device, such as the needle 98, from the arcuate slot 12 of the guidance device 10. For example, see FIG. 8.

A straight cannula with a tapered dilator is passed over the flexible trocar and inserted down to the wall of the annulus. The position of the cannula and the position of the flexible trocar is again verified by the C.T. scanner S.

An incision is made of the annulus by a trephine, and then the trephine and flexible trocar are removed from the cannula.

The nucleotome probe is inserted through the cannula into the nucleus pulposus, and the correct position is verified by overhead films on the C.T. scan table T.

Suction of the annulus pulposus is performed for approximately 25 minutes. After completion, the patient returns home the same day of the procedure.

USE OF THE STEREOTACTIC DEVICE IN COMBINATION WITH THE STEREOTACTIC BRIDGE (STEREOTACTIC BRIDGE-SUPPORTED MODE)

The patient is placed on the C.T. scan table T in the prone position. The lumber region is prepped and draped in the usual manner.

The table top carrying the patient is moved into the gantry opening O and thin 3-5 mm axial tomographic cuts are obtained by C.T. scan through the herniated disc.

The best tomographic cut is selected and a transverse light beam line identical to the tomographic cut with an X-ray beam is made on the patient and marked on the skin with a colored line.

The point of entrance is marked with the needle 98 and determined by the C.T. scan. The depth and angle are determined by C.T. scan guidance.

The table top carrying the patient is removed from the gantry opening O. The position of the patient on the table top should not be changed in order to maintain the torso in the same position that the torso was in at the time that the best tomographic cut was taken.

Local anesthesia is administered in the skin, muscles and paravertebral space and a 3 mm in diameter skin incision is made at the selected point of entry for the flexible trocar.

The stereotactic bridge is affixed to the C.T. scan table T below the movable table top. The bridge can be considered an accessory to the C.T. scan table. The span 100 of the bridge supports and orients the guidance device 10, as shown in FIG. 1. As seen in FIG. 7, the device 10 is situated with the cutout portion 50 defining the sterile field over the skin incision. As shown in FIG. 4, a level 60 on the device 10 is used to assure horizontal positioning of the stabilizing table. If a level 60 is on the base 15, then that level 60, as shown in FIGS. 10 and 13, may be checked to verify horizontal positioning. The device 10 is aligned and optionally locked on the span 100, 200, 300, or 400. Where the C.T.-generated tomographic cut is made using a sagittal orientation, the span 100, 200, 300, or 400 is rotated using a means for measuring axial rotation in order to orient the plane of medical device insertion at the exact sagittal orientation of the tomographic cut. See FIG. 6 again.

The flexible trocar is inserted with a single pass into the point of interest. The device 10 is removed and the patient is moved with the table top of the gantry to the original position. Verification of the position of the flexible trocar is made by C.T. scan. It is important for the patient not to move on the table top during this part of the procedure.

A straight cannula with a tapered dilator is passed over the flexible trocar and is inserted down to the wall of the annulus. The position of the cannula and the position of the flexible trocar are again verified by C.T. scan.

Incision of the annulus is made by the trephine, and then the trephine and the flexible trocar are removed from the cannula.

The nucleotome probe is inserted through the cannula into the nucleus pulpous and the correct position is checked by overhead films on the C.T. scan table T.

Suction of the annulus pulpous is performed for approximately 25 minutes. Thereafter, the patient returns home the same day of the procedure.

In this procedure, it should be noted that verification of the needle position can alternatively be made utilizing an X-ray machine appropriately oriented.

Moreover, the stereotactic bridge and the guidance device 10 in combination allow for rapid and precise multiple verification sequences where the procedure is extended and requires repetitive position verification.

Any means for affixation of a protractor to the bridge may be used. One essential aspect of the invention is that a guidance device 10, comprised of the protractor 30 and the associated medical device carrier 20, can be affixed to the bridge so that, in conjunction, movement, orientation, and stability are achieved. Accordingly, the means specified for the function of the guidance device 10, as it will be appreciated, can be modified without departing from the scope of the invention described and claimed herein.

From the foregoing description, it will be apparent that the invention permits simple yet positive orientation of the various medical devices, such as the needles 98 described herein. When the proper orientation has been determined, the guidance device 10 may be locked and will then serve to guide the needle 98 or cannula to the desired region of the body.

While preferred embodiments of the invention have been shown and described, it will be apparent to those skilled in the art that changes can be made without departing from the principles and spirit of the invention, the scope of which is defined in the appended claims. Accordingly, the foregoing embodiments are to be considered illustrative, rather than restrictive of the invention, and those modification which come within the meaning and range of equivalency of the claims are considered to be included therein.

What I claim as my invention is:

1. A stereotactic device comprising:
   a. a base having an upper surface exposed when the stereotactic device is in use and a lower surface for placement on a body into which a medical device is to be introduced through a sterile field, said base having an opening therein, through which a part of the medical device to be placed within the body can pass unobstructed;
   b. a leg normal to the base, affixed thereto and having a radial slot therein;
   c. a carrier for the medical device comprising:
      i. a radial portion which rides within the radial slot;
      ii. retaining means for retaining the medical device in a fixed radial position relative to an arc defined by the radial slot and downwardly through the opening in the base, said retaining means being selectively openable such that the medical device can be laterally placed in and removed from the carrier;
      iii. means for locking said carrier at a fixed position on an arcuate pathway formed by the slot; and
   d. markings on said leg along said radial slot for placement of the retaining means at a preselected point along said radial slot whereby the medical device retained thereby can be extended downwardly through the opening and into the body at a preselected angle;
   wherein the base comprises opposing edges normal to the leg, said edges being beveled and sloping downwardly and outwardly from the upper surface of the base; and further comprising markings on said base for orienting said base on the body, said markings on said base comprising markings on said beveled edges.

2. The stereotactic device of claim 1, wherein the angle of the bevel, at the opposing edges, is from about 15 degrees to about 75 degrees.

3. A stereotactic device comprising:
   a. a base having an upper surface exposed when the stereotactic device is in use and a lower surface for placement on a body into which a medical device is to be introduced through a sterile field, said base having an opening therein, through which a part of the medical device to be placed within the body can pass unobstructed;
   b. a leg normal to the base, affixed thereto and having a radial slot therein;
   c. a carrier for the medical device comprising:
      i. a radial portion which rides within the radial slot;
      ii. retaining means for retaining the medical device in a fixed radial position relative to an arc defined by the radial slot and downwardly through the opening in the base, said retaining means being selectively openable such that the medical device can be laterally placed in and removed from the carrier;
      iii. means for locking said carrier at a fixed position on an arcuate pathway formed by the slot; and
   d. markings on said leg along said radial slot for placement of the retaining means at a preselected point along said radial slot whereby the medical device retained thereby can be extended downwardly through the opening and into the body at a preselected angle;

wherein the base is made of a transparent material, markings are on the upper surface of said base and run along at least a portion of the length of the upper surface of the base in parallel with the leg.

4. The stereotactic device of claim 3, wherein the stereotactic device is T-shaped and the leg of said stereotactic device divides said base into a first part delimiting the sterile field and a second part remote from the sterile field and separated therefrom by said leg, said stereotactic device further characterized in that said markings on the base of said device are for orientation of said base on the body.

5. The stereotactic device of claim 4, wherein a leveling means is connected to the stereotactic device for assisting in orienting a longitudinal axis of the base horizontally.

6. The stereotactic device of claim 5, wherein the leveling means is a circular bubble level secured on the upper surface of the base.

7. A stereotactic medical device for accurate placement of a medical instrument in a plane of horizontal or sagittal orientation comprising:
 a. a stereotactic bridge comprising:
  (i) a span configured to overly a body;
  (ii) stanchions supporting said span;
  (iii) means for moving said span vertically up and down said stanchions; and
  (iv) means for moving said stanchions horizontally along at least a portion of the length of the body overlaid by the span;
 b. a guidance device for accurate introduction of a part of medical instrument of a given length into said body, said guidance device comprising:
  (i) a base comprised of a plate and an upstanding leg positioned substantially perpendicular to the plate, said plate on one side of said upstanding leg having a cutout opening delimiting a sterile field through which a part of the medical instrument can pass unobstructed into a predetermined part of the patient's body and on the other side of said upstanding leg, said plate having a means for connecting said guidance device to said span of said stereotactic bridge, said leg comprised of an arcuate track with means therealong for indicating a plurality of preselected angles relative to the predetermined part of the patient's body which is accessible through the opening in the plate;
  (ii) a carrier including riding means for movement along the arcuate track, retaining means for retaining the medical instrument in a fixed position relative to the riding means, and means for locking the retaining means at one of the preselected angles relative to the predetermined part of the body, wherein said retaining means is selectively openable such that the medical device can be laterally placed in and removed from the carrier; and
  (iii) means for axially rotating the guidance device in correlation with an angulation of a C.T. scanner to enable sagittal insertion of the medical instrument;
  whereby the part of the medical instrument retained by the carrier can be extended through the opening in the plate and into the predetermined part of the body at said one of the preselected angles;
 c. means for moving and locking the guidance device along the length of said span, said means including said means for connecting said guidance device to said span of said stereotactic bridge.

8. The medical device of claim 7, wherein the movement of the span vertically up and down the stanchions is facilitated by means of a negator spring.

9. The medical device of claim 8, wherein the axis of rotation of the guidance device pivots on a centerline which intersects the point of entry of the medical instrument into the body.

10. The medical device of claim 7 further comprising a means for leveling the guidance device after the guidance device is connected to the span.

11. The medical device of claim 10 wherein said leveling means is a leveling bubble on the guidance device on the span.

12. The medical device of claim 11, wherein the axis of rotation of the guidance device pivots on a centerline which intersects the point of entry of the medical instrument into the body.

13. The medical device of claim 10, wherein the axis of rotation of the guidance device pivots on a centerline which intersects the point of entry of the medical instrument into the body.

14. The medical device of claim 7, wherein the arcuate track is an arcuate slot of a given width cut through said leg and the means for movement along the arcuate track comprises a means for riding within the arcuate slot cut through the leg.

15. The medical device of claim 14, wherein the retaining means of the guidance device is a pair of arms with threaded bores therethrough and spaced from each other at a distance less than a given length of the medical instrument so that said medical instrument can be held securely in the bores thereof.

16. The medical device of claim 15, wherein the means for moving and locking the carrier includes a threaded fastener means for engaging a threaded bore through a cylindrical protrusion of the riding means.

17. The medical device of claim 16, wherein the axis of rotation of the guidance device pivots on a centerline which intersects the point of entry of the medical instrument into the body.

18. The medical device of claim 15, wherein the axis of rotation of the guidance device pivots on a centerline which intersects the point of entry of the medical instrument into the body.

19. The medical device of claim 14, wherein the axis of rotation of the guidance device pivots on a centerline which intersects the point of entry of the medical instrument into the body.

20. The medical device of claim 7, wherein the axis of rotation of the guidance device pivots on a centerline which intersects the point of entry of the medical instrument into the body.

* * * * *